United States Patent [19]

Wanderer et al.

[11] Patent Number: 4,731,059

[45] Date of Patent: Mar. 15, 1988

[54] COMBINATION NEEDLE SHIELD/NEEDLE GUARD DEVICE POSITIVELY LOCKED ONTO DETACHABLE NEEDLE ASSEMBLIES FOR AN EVACUATED BLOOD COLLECTION SYSTEM AND A HYPODERMIC SYRINGE

[75] Inventors: Alan A. Wanderer, Englewood; William E. Sagstetter, Denver, both of Colo.

[73] Assignee: Medical Safety Products, Inc., Denver, Colo.

[21] Appl. No.: 918,020

[22] Filed: Oct. 14, 1986

[51] Int. Cl.$^4$ ............................................ A61B 5/14
[52] U.S. Cl. .................................... 604/192; 604/110; 604/198; 128/764; 128/765
[58] Field of Search ............... 604/110, 162, 163, 192, 604/197, 198, 201, 205, 206, 240–243, 272–274, 413, 414, 263; 128/763–765; 206/363–366, 438, 571

[56] References Cited

U.S. PATENT DOCUMENTS

| | | | |
|---|---|---|---|
| 2,997,043 | 8/1961 | Flynn | 604/263 |
| 3,134,380 | 5/1964 | Armao | 604/198 |
| 3,380,448 | 4/1968 | Sadove et al. | 604/263 |
| 3,989,044 | 11/1976 | Meierhoefer | 604/192 |
| 4,113,090 | 9/1978 | Carstens | 206/365 |
| 4,170,993 | 10/1979 | Alvarez | 604/263 |
| 4,453,936 | 6/1984 | Cassou | 604/263 |
| 4,573,976 | 3/1986 | Sampson et al. | 604/198 |
| 4,643,722 | 2/1987 | Smith, Jr. | 604/263 |
| 4,654,034 | 3/1987 | Masters et al. | 604/263 |
| 4,655,751 | 4/1987 | Harbaugh | 604/198 |
| 4,659,330 | 4/1987 | Nelson et al. | 604/192 |

*Primary Examiner*—Dalton L. Truluck
*Assistant Examiner*—F. Wilkens
*Attorney, Agent, or Firm*—Cahill, Sutton & Thomas

[57] ABSTRACT

This invention relates to a combination needle shield/needle guard device that is positively locked onto detachable needle assemblies for an evacuated blood collection system and for a hypodermic syringe. More particularly, this invention can: (1) function as a needle shield to enclose and prevent contamination of the sterile needle to be used for a medical procedure; (2) function as a needle guard which can slide on a length extension for either needle assembly, such that the needle can be uncovered or re-covered in a direction from behind the needle point, thereby providing a safety feature for the operator who can avoid direct contact with a used, blood-contaminated needle point. Avoidance of direct contact with used needle points will reduce the likelihood of contracting blood-borne infections such as AIDS, infectious hepatitis, syphilis etc. that might occur following accidental puncture with contaminated needles; (3) provide improved securing for an evacuated blood collection system between the double-ended needle assembly and the container holder, thereby preventing the double-ended needle assembly from unlocking with the container holder during the process of withdrawing blood into an evacuated container and (4) improve blood withdrawing success with the blood evacuated collection system and with a large volume syringe. This occurs by the addition of a length extension which separates the wide girth of the container holder or the wide girth of a large volume syringe barrel from close approximation to the needle used for withdrawing blood, thereby permitting more shallow or acute angle access of needle entry into a blood vessel during blood withdrawing procedures.

45 Claims, 31 Drawing Figures

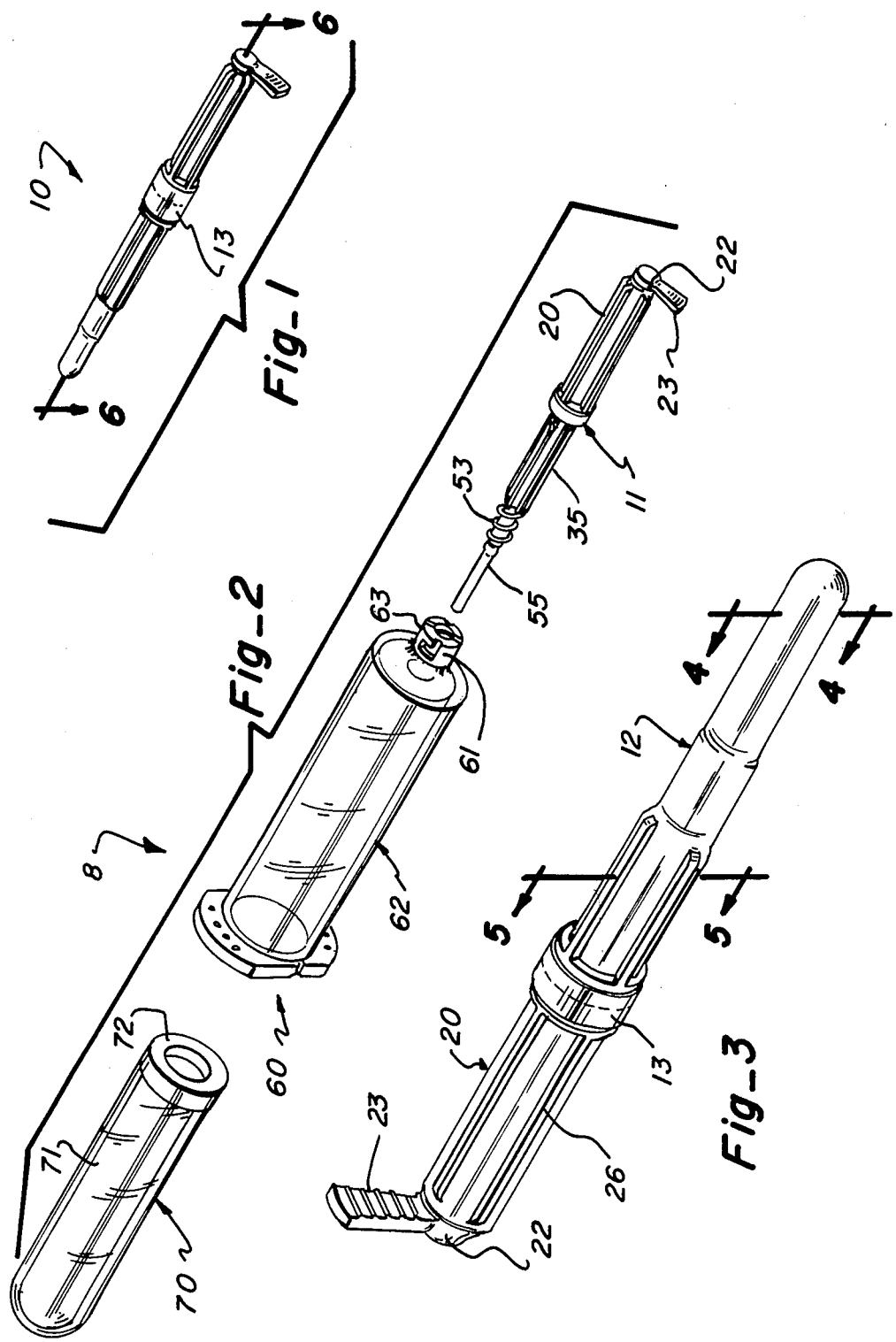

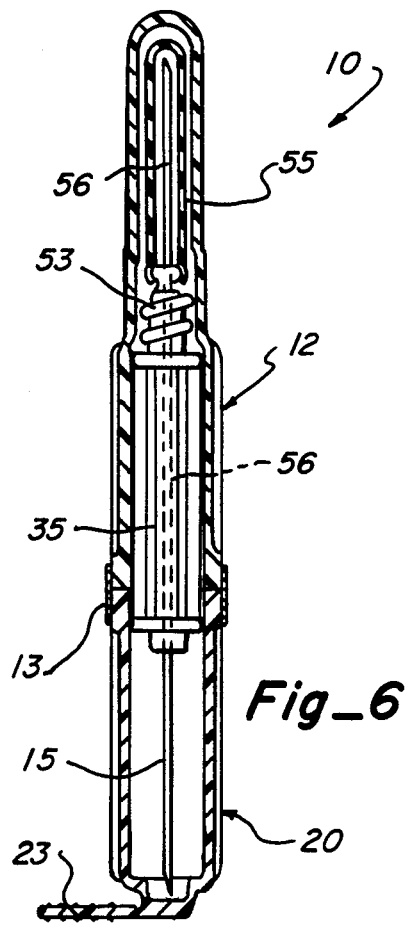
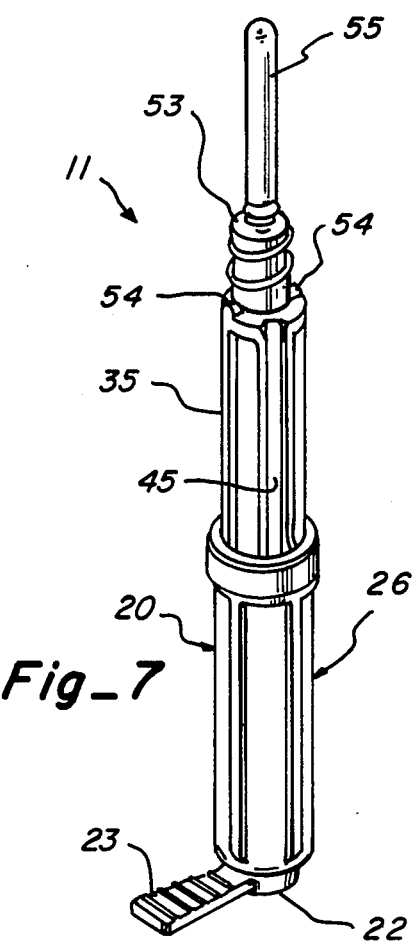
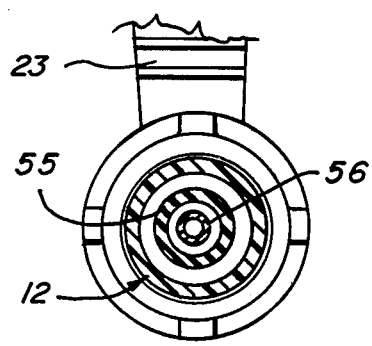
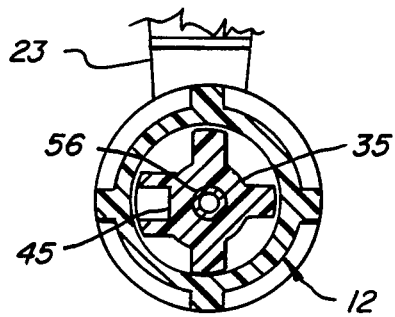
Fig_6
Fig_7
Fig_4
Fig_5

U.S. Patent  Mar. 15, 1988  Sheet 3 of 7  4,731,059
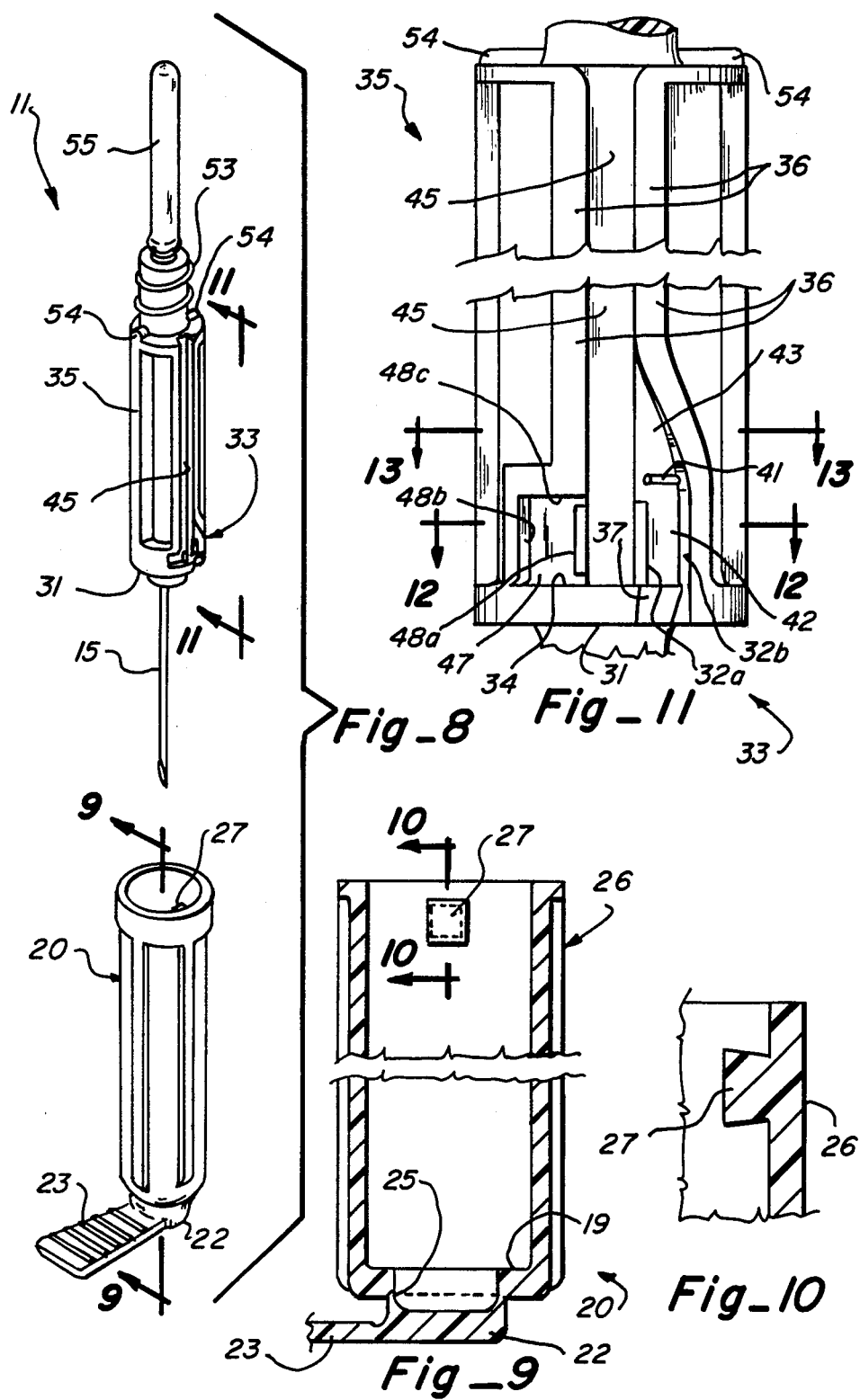

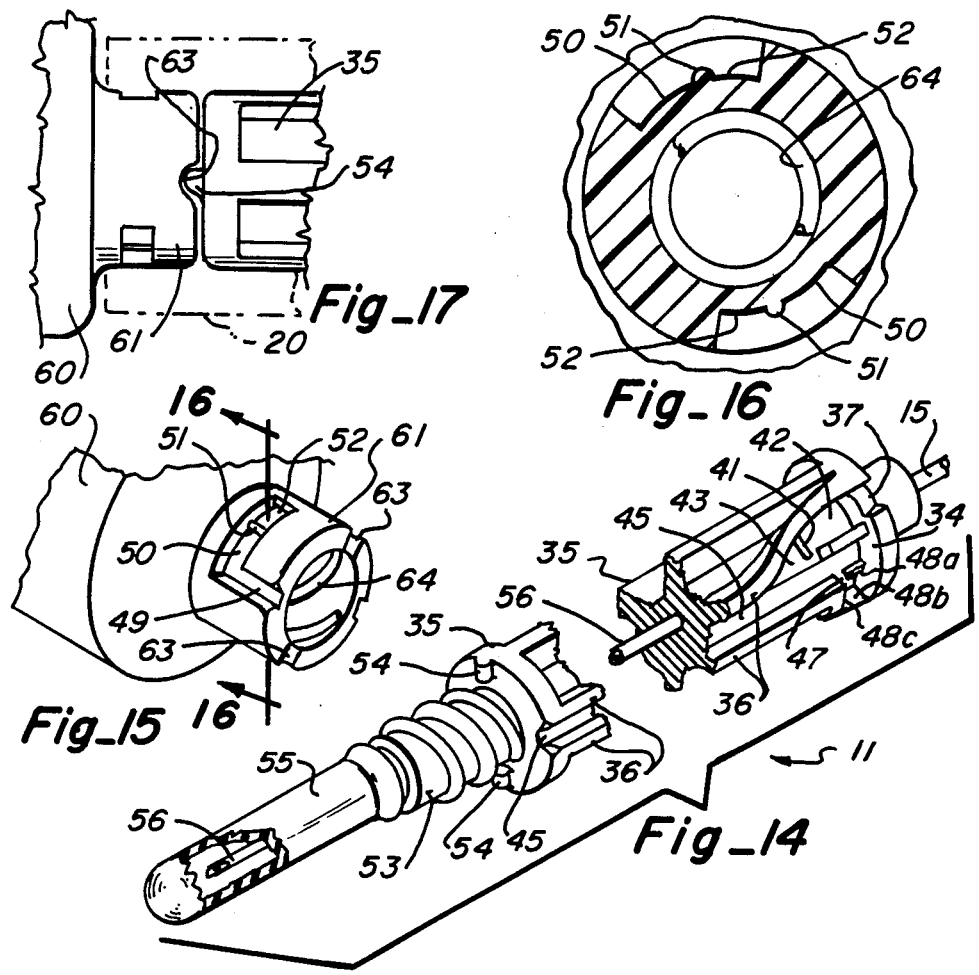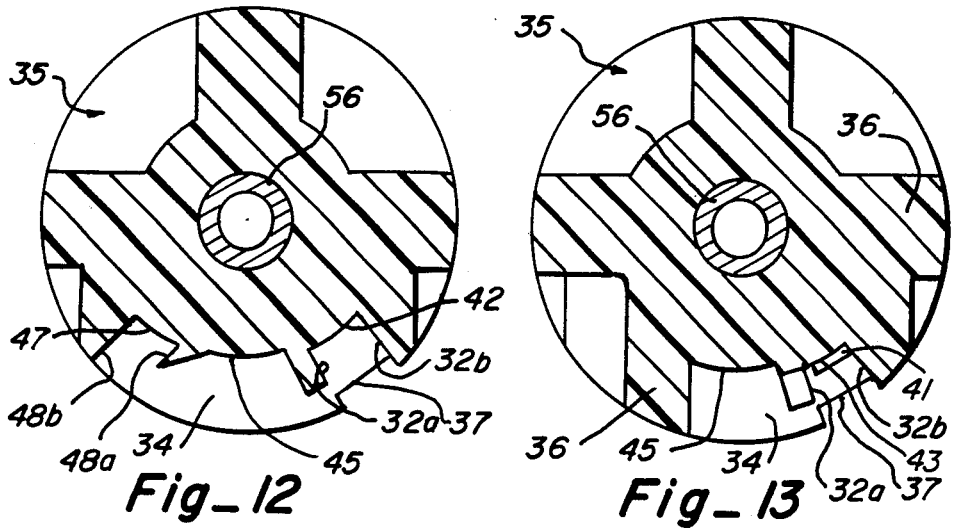

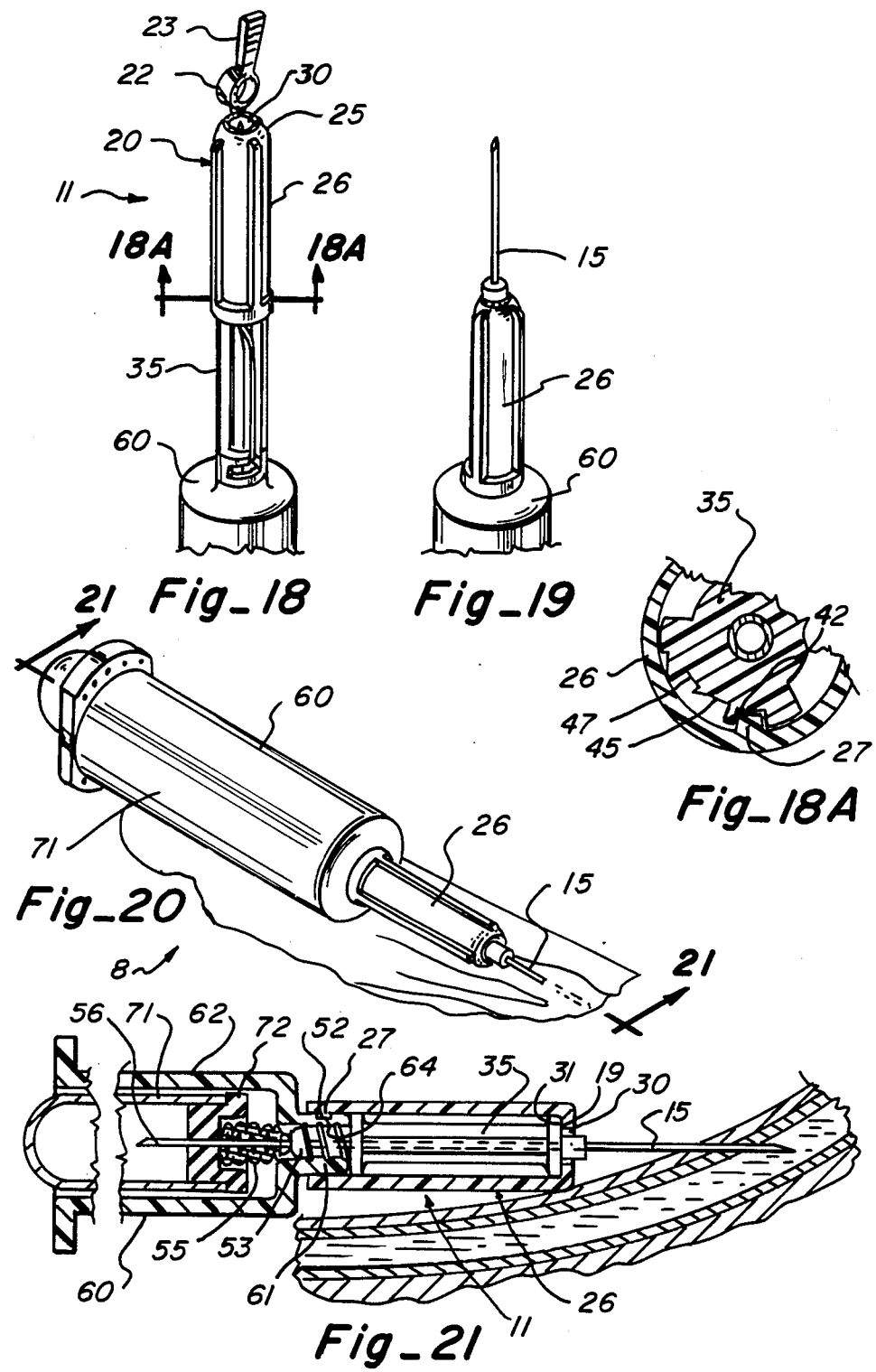

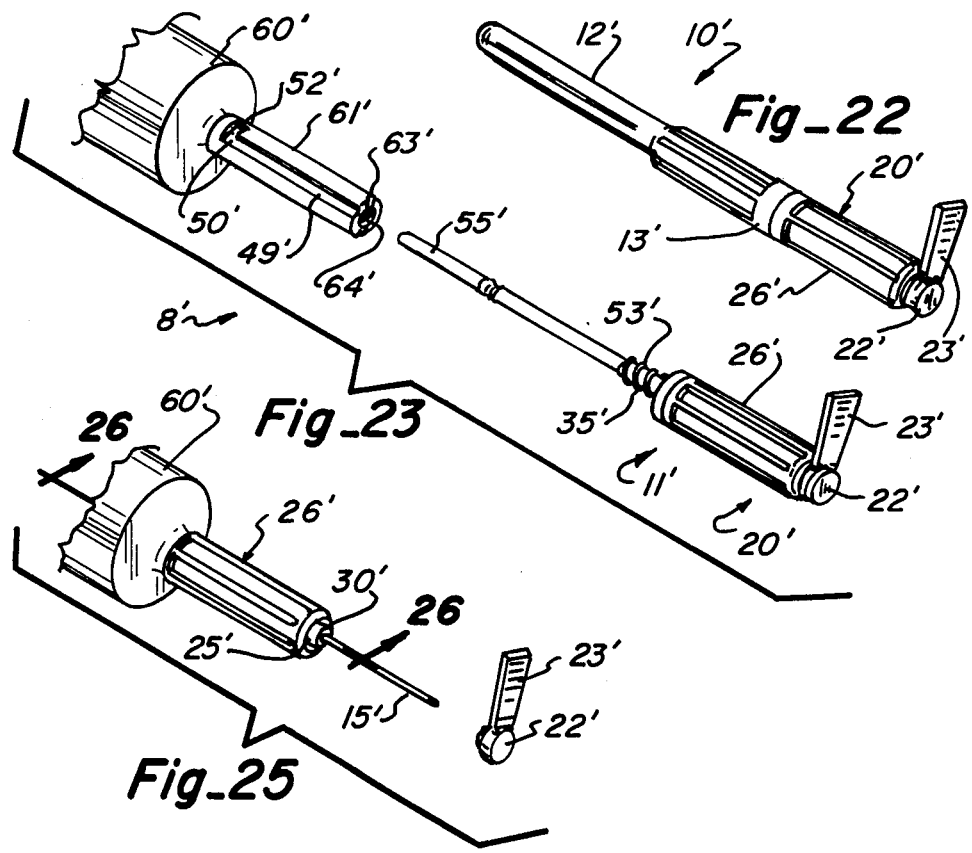
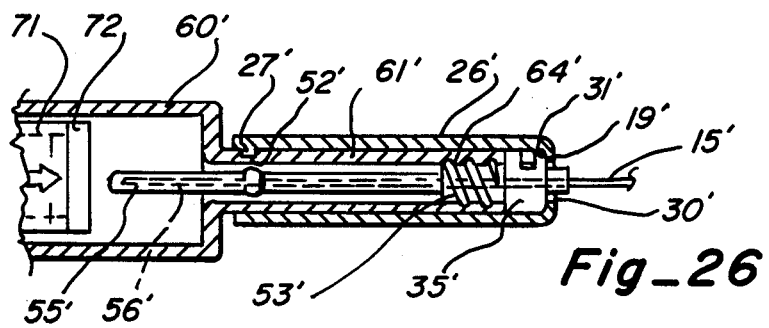
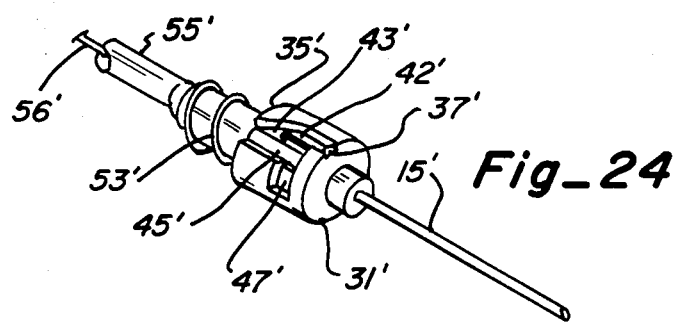

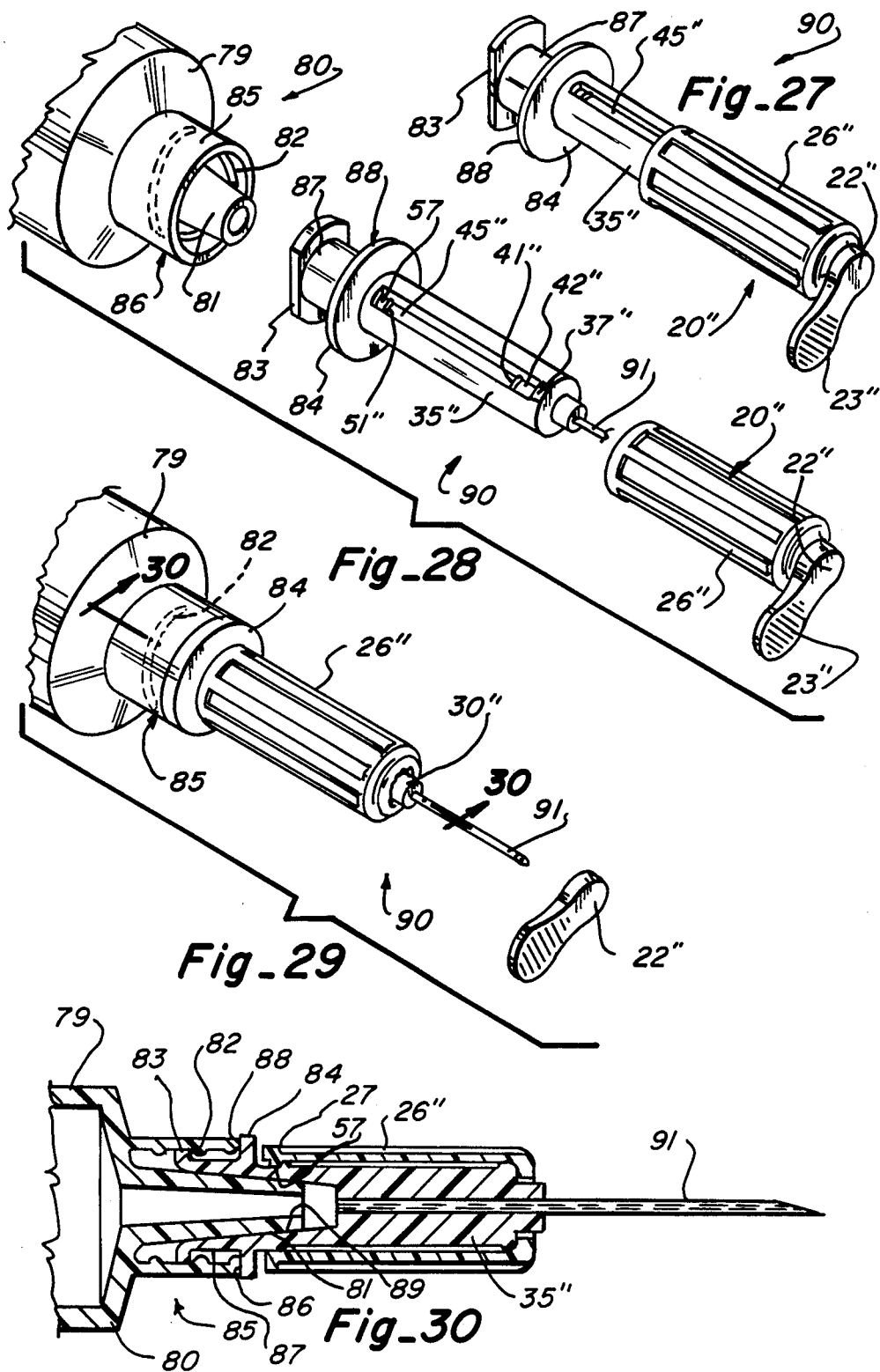

COMBINATION NEEDLE SHIELD/NEEDLE GUARD DEVICE POSITIVELY LOCKED ONTO DETACHABLE NEEDLE ASSEMBLIES FOR AN EVACUATED BLOOD COLLECTION SYSTEM AND A HYPODERMIC SYRINGE

BACKGROUND OF THE INVENTION

1. Field of the Invention

This invention relates to a combination needle shield/needle guard device which is positively locked onto a (1) detachable double-ended needle assembly used for an evacuated blood collection system and (2) a detachable needle assembly for a hypodermic syringe. More particularly, this combination needle shield/needle guard device can function as a needle shield to enclose and prevent contamination of a sterile needle to be used for insertion into the skin and/or blood vessel of a patient. In addition, the needle shield/needle guard device can function as a needle guard which can slide on the needle assemblies, so that the needle can be uncovered or re-covered in a direction from behind the needle point, thereby providing a safety feature for the operator who can avoid direct contact with a used, blood-contaminated needle point.

2. Description of the Prior Art

There are many types of removeable needle shields which cover needles used with conventional syringes or are used to cover a double-ended needle assembly with an evacuated blood collection system. Examples include the following references selected from the U.S. Patent and Trademark Office: U.S. Pat. Nos. 3,381,813; 3,934,722; 4,113,090; 4,121,588; 3,734,080; and 3,931,815. These removeable needle shields reveal several limitations such as: (1) after removal of the needle shield from the needle attached to a syringe, medical personnel may occasionally delay the usage of the needle in a procedure, which would require replacement of the needle shield back over the needle to prevent contamination of the sterile needle. This maneuver requires keeping track of the removed needle shield and then replacing the needle shield over the needle, which represent extra steps for busy medical personnel. Replacing the needle shield over the needle point also increases the risk for self-puncture with the needle point; (2) another common practice occurs when medical personnel remove this type of needle shield by holding the needle shield between their teeth or lips. This maneuver has been associated with accidental self-puncture in the face or other bodily parts; (3) in order to remove a used double-ended needle assembly from a reuseable container holder of an evacuated blood collection system, it is necessary to re-cover the used needle with a needle shield and then unfasten the double-ended needle assembly from the reusable container holder. Similarly, to remove a used needle that is luer-locked to a syringe barrel, it is necessary to re-cover the needle with a needle shield and then unfasten the needle from the syringe barrel. Both procedures require that the user replace the needle shield over the pointed end of the used needle, which increases the risk to medical personnel who may accidentally puncture themselves with the pointed end of the used, blood contaminated needle; (4) when the needle shield is replaced over the used needle, if the needle has been accidentally bent during a medical procedure or if the needle shield is replaced over the needle at an incorrect angle, the needle point may inadvertently pierce the side of the needle shield as it is being replaced over the needle. The operator using the needle shield could be punctured with a used blood-contaminated needle point that has exteriorized through a needle shield; and (5) most laboratories use containers with or without a clip-off needle device to store used needles. Personnel may puncture themselves with used uncovered needles that may accidentally fall out of these storage containers or with uncovered needles that are disposed of inappropriately in waste baskets. In addition, if the storage container is full, it is possible to accidentally puncture oneself with a used, uncovered needle that is pointed towards the opening of the storage container.

Another device relevant to our invention includes U.S. Pat. No. 4,425,120 issued to Sampson et al which describes a needle guard device which is attached to a conventional hypodermic syringe or apparatus used for injecting a substance into a human or animal. This device functions as a slideable needle guard to uncover or re-cover a used needle. This needle guard has an open-end, which precludes its routine use to function also as a needle shield to enclose and prevent contamination of a sterile needle. In order to prevent contamination of the sterile needle in this device, it would be necessary to cover the needle with a separate needle shield, or close the opening of the needle guard with a material which must be ruptured by the needle or needle shield enclosing the needle. In addition, this needle guard device is not adapted to remove a used double-ended needle assembly from a container holder or to remove a used hypodermic syringe needle assembly from a syringe barrel. Thus, in both situations a separate needle shield would still be required to re-cover and unfasten the detachable needle assemblies, thereby increasing the risk for self-puncture with a used needle point.

Another needle guard device, U.S. Pat. No. 4,139,009 issued to Alvarez, is composed of four longitudinal arms which are brought into lateral side-to-side contact with the intention of covering and protecting the enclosed needle. The front end of the cover and the lateral arms in side-to-side contact represent discontinuous locations which could permit microorganism penetration and contamination of the enclosed sterile needle. When this device is pushed against a skin surface during the injection process, the arms must bow away from the longitudinal axis of the needle which could block visualization of the needle as it penetrates the skin. It is important that the operator attempting to draw blood be able to clearly visualize a blood vessel. In addition, this needle guard device is not adapted to remove a used double-ended needle assembly from a container holder or to remove a used needle assembly from a hypodermic syringe barrel. Thus, in both situations a needle shield would still be required to re-cover and unfasten the detachable needle assemblies, thereby increasing the risk for self-puncture with a used needle point.

Examples in the U.S. Patent and Trademark Office of evacuated blood collection systems with a removeable needle shield are U.S. Pat. Nos. 2,460,641, 3,931,815, 4,154,229, 4,295,476, 4,295,477, 4,312,362, and 4,340,068. Operators of a blood evacuated collection system with a double-ended needle assembly must re-cover a used needle over the pointed end of the needle with a needle shield in order to unfasten the double-ended needle assembly from the reusable container holder. This maneuver can cause puncture with contaminated needles with the subsequent risk of developing blood-borne infections, such as AIDS, infectious hepatitis, syphilis, etc. Similar risks occur for the operator of a hypodermic syringe who must replace a needle shield over the detachable needle assembly in order to remove the used needle from the syringe barrel. Therefore during the procedure of removing used needle assemblies from an evacuated blood collection system or hypodermic syringe, it is desireable to provide a mechanism whereby the operator of either device can be safeguarded from causing self-puncture with a used, blood contaminated needle point.

There are other identifiable problems with currently used blood evacuation collection systems. The container holder used in the blood evacuated collection system exhibits several limitations that can interfere in successful blood withdrawing procedures. On occasion operators of an evacuated blood collection system have experienced the unfortunate occurrence in which the double-ended needle assembly has unfastened from the container holder. This may occur during the following circumstances: (1) the first needle of the double-ended needle assembly has penetrated into a blood vessel; (2) the operator has begun to move an evacuated container forward into the container holder so that the inner needle (i.e. second needle) of the double-ended needle assembly can penetrate through the evacuated container stopper; (3) during step 2, the force of pushing on the second needle causes the threads on the housing of the double-ended needle assembly to unwind from the internal mating threads at the forward end of the container holder, thereby causing the entire double-ended needle assembly to disengage from the container holder. There are several explanations for the disengagement of these parts such as: (1) the threads of the housing of the double-ended needle assembly are not tightened properly into the internal mating threads of the container holder; and/or (2) the internal mating threads of the container holder can become worn from frequent usage which would subsequently prevent adequate securing between the housing of the double-ended needle assembly and the container holder. It is thus desireable to provide a mechanism to eliminate this problem by using an improved locking system between the double-ended needle assembly housing and the container holder.

Another problem which develops using a blood evacuated collection system concerns the positioning of the first needle into a blood vessel. The wide girth of the container holder can cause the operator to direct the needle in a less acute angulation in respect to the planar surface of the skin, thereby causing the needle point to puncture the blood vessel wall at a higher, less acute angle that will more easily lead to puncturing through the opposite wall of the blood vessel. If such an event occurs, it may be difficult to withdraw blood from the blood vessel, as well as cause subsequent blood leakage around the blood vessel i.e. hematomas. A similar problem can occur for the user of a hypodermic syringe, especially for large volume syringes with a wide diameter of the syringe barrel. It is therefore desireable to eliminate the configuration restrictions imposed by a wide girth container holder or barrel of a hypodermic syringe which make it difficult for the operator to direct the needle in a more shallow or acute angle in respect to the planar surface of the skin.

SUMMARY OF THE INVENTION

The embodiments of this invention have been developed: (1) as a needle shield to enclose and prevent contamination of the sterile needle to be used for insertion into a patient's skin or blood vessel; (2) as a moveable needle guard which is capable of protecting medical personnel from puncturing themselves with contaminated needle points, since the needle can be re-covered by moving the device from behind the used needle point. This feature will reduce the associated risk of contracting blood-borne infections such as AIDS, hepatitis, syphilis, etc. It is important to emphasize that our device can function both as a needle shield and as a needle guard, thus providing a distinct advantage over prior art which includes devices that serve only one of these functions. In addition, manufacturing costs could be reduced with our needle shield/needle guard device which requires one part to perform both aforementioned functions; (3) to eliminate the need of keeping track of a removeable needle shield, which has led to the common practice among busy personnel who may remove this type of needle shield by holding the needle shield between their teeth or lips. In our device the needle shield/needle guard device is positively locked onto the double-ended needle assembly or hypodermic needle assembly so that it is readily available to the user of the device; (4) to re-cover used blood contaminated needles, such that when used needles are disposed of in containers they will always be re-covered with the device; (5) to unfasten the used double-ended needle assembly from the reusable container holder of an evacuated blood collection system or to unfasten a used hypodermic needle assembly from a hypodermic syringe barrel without the user needing to replace a separate needle shield over the pointed end of a used needle. Our device therefore provides an important safeguard since it reduces the hazard of self-puncture for the user who does not have to replace a removeable needle shield backover a used needle point; and (6) in addition, this invention provides a positive lock to permanently cover the used needle of an evacuated blood collection system, so that after the needle has been used to withdraw blood, it can not be used inadvertently on another patient.

Other advantages of our invention include: (7) it can assist medical personnel using a hypodermic syringe, who may need to delay a medical procedure and thus must temporarily re-cover the unused needle. This need can be facilitated by moving an easily accessible, non-removeable needle shield/needle guard device back over the sterile needle to prevent contamination of the unused sterile needle; (8) our invention for an evacuated blood collection system provides additional secondary and tertiary locking means between the double-ended needle assembly and the container holder which prevent disengagement between these parts during the blood withdrawing procedure; and (9) the length extension that occurs between the needle used to withdraw blood and the body of the container holder of an evacuated blood collection system or the analogous length extension that occurs between the needle of a hypodermic needle assembly and the wide diameter of a syringe barrel, allow for more favorable angulation of needle penetration into a patient's blood vessel. The narrow diametered length extensions eliminate the configuration restriction caused by the wide girth of the container holder or by the wide diameter of a large volume syringe barrel, thereby permitting the user to direct the needle into the blood vessel at a more shallow or acute angle in respect to the planar surface of the skin, thus minimizing the chance of piercing through the other side of the blood vessel wall.

Other objectives and advantages of our invention will become apparant more fully from the following description and accompanying drawings illustrating the embodiments of the device.

BRIEF DESCRIPTION OF THE DRAWINGS

FIG. 1 is an isometric view illustrating a sterile package container of the double-ended needle assembly for the first embodiment of the evacuated blood collection system.

FIG. 2 is an exploded isometric view of the components of the first embodiment of the evacuated blood collection system.

FIG. 3 is an enlarged isometric view of a sterile package container of the first embodiment of the evacuated blood collection system.

FIG. 4 is a cross-sectional view of FIG. 3 along line 4—4.

FIG. 5 is a cross-sectional view of FIG. 3 along line 5—5.

FIG. 6 is a full longitudinal section along line 6—6 of FIG. 1.

FIG. 7 is an enlarged isometric view of the first embodiment of the double-ended needle assembly with the needle shield/needle guard device.

FIG. 8 is an exploded isometric view of the first embodiment of the double-ended needle assembly with the needle shield/needle guard device.

FIG. 9 is a longitudinal sectional view along line 9—9 in FIG. 8.

FIG. 10 is a longitudinal section along line 10—10 in FIG. 9.

FIG. 11 is a fragmented side view along line 11—11 in FIG. 8.

FIG. 12 is a cross-sectional view along line 12—12 of FIG. 11.

FIG. 13 is a cross-sectional view along line 13—13 of FIG. 11.

FIG. 14 is an enlarged partial isometric view of the first embodiment of the double-ended needle assembly without the needle shield/needle guard device.

FIG. 15 is an enlarged view of the proximal end of the container holder for the first embodiment of the evacuated blood collection system.

FIG. 16 is a cross-sectional view of FIG. 15 along line 16—16.

FIG. 17 is a fragmented side view of first embodiment of the evacuated blood collection system illustrating the secondary locking means for fastening of double-ended needle assembly to container holder.

FIG. 18 is a fragmented isometric view of the needle shield/needle guard device positioned in the first extended lock position on the first embodiment of the double-ended needle assembly.

FIG. 18A is a cross-sectional view along line 18A—18A of FIG. 18.

FIG. 19 is a fragmented isometric view illustrating the cylindrical housing of the needle shield/needle guard device positioned in the retracted lock position on the first embodiment of the double-ended needle assembly.

FIG. 20 illustrates the first embodiment of the evacuated blood collection system in which the cylindrical housing of the needle shield/needle guard device is retracted on the double-ended needle assembly, exposing the first needle during venipuncture use.

FIG. 21 is a longitudinal section along line 21—21 in FIG. 20.

FIG. 22 is an isometric view illustrating a sterile package container of the double-ended needle assembly for the second embodiment of the evacuated blood collection system.

FIG. 23 is a partial exploded isometric view of the second embodiment of the evacuated blood collection system.

FIG. 24 is an enlarged partial isometric view of the double-ended needle assembly without the needle shield/needle guard device for the second embodiment of the evacuated blood collection system.

FIG. 25 is a partial isometric view of the second embodiment of the evacuated blood collection system, illustrating the removal of the pull-off tab from the needle shield/needle guard device and the exposure of the needle by retracting the cylindrical housing of the needle shield/needle guard device on the double-ended needle assembly.

FIG. 26 is a longitudinal sectional view along line 26—26 of FIG. 25.

FIG. 27 is an isometric view of the detachable needle assembly for a hypodermic syringe.

FIG. 28 is a partial exploded view of the first embodiment of the detachable needle assembly and hypodermic syringe.

FIG. 29 is a partial isometric view of the first embodiment of the detachable needle assembly and hypodermic syringe, illustrating the removal of the pull-off tab from the needle shield/needle guard device and the exposure of the needle by retraction of the cylindrical housing of the needle shield/needle guard device on the needle assembly.

FIG. 30 is a longitudinal sectional view along line 30—30 of FIG. 29.

DETAILED DESCRIPTION

Detailed drawings are shown for a first and second embodiment of an evacuated blood collection system and for a first embodiment of a detachable needle assembly for a hypodermic syringe. This disclosure is made with the understanding that the present disclosure is to be considered as exemplary of the principles of the invention and are not intended to be limited only to the illustrated embodiments.

Referring to the drawings, FIGS. (1 to 21) refer to the first embodiment 8 of the blood evacuation collection system. FIG. 1 illustrates a sterile package container 10 for the double-ended needle assembly 11 that is used (see FIG. 2) in the first embodiment 8 of an evacuated blood collection system. The basic components of the sterile package container 10 are seen in an enlarged isometric view in FIG. 3 and includes the needle shield/needle guard device 20 comprised of cylindrical housing 26 and pull-off tab 22 with handle 23, a second needle shield 12, and sterile sealing tape 13 which joins and seals the attachment of the needle shield/needle guard device 20 to the second shield 12. FIGS. 4 and 5 represent cross-sectional views of FIG. 3 along lines 4—4 and 5—5 respectively. FIG. 4 illustrates the second needle 56 of the double-ended needle assembly 11, the self-recoverable elastic sheath 55, and the needle shield 12 for the second needle 56. FIG. 5 illustrates the second needle 56 covered in the extended housing 35, the longitudinal groove 45 on the extended housing 35, and the needle shield 12. FIG. 6 is a full longitudinal section of the sterile package container 10 seen in FIG. 1 along line 6—6. This illustrates the enclosed double-ended needle assembly 11 (see FIG. 2) which is comprised of needle shield/needle guard device 20 which encloses first needle 15, second needle shield 12 which encloses second needle 56 which in turn is enclosed by self-recoverable elastic sheath 55, extended housing 35, double lead-in external threads 53 on extended housing 35, and sterile sealing tape 13 which joins and seals the attachment of the needle shield/needle guard device 20 to the second shield 12. FIG. 7 illustrates the double-ended needle assembly 11 for the first embodiment 8 of the evacuated blood collection system seen in FIG. 2 with the second shield 12 removed. FIG. 7 reveals the needle shield/needle guard device 20 comprised of cylindrical housing 26 with pull-off tab 22, extended housing 35 with longitudinal groove 45, double external protrusions 54 on extended housing 35, double lead-in external threads 53 and self-recoverable elastic sheath 55 covering second needle 56.

FIG. 8 is an exploded isometric view of the double-ended needle assembly 11 for the first embodiment 8 of the evacuated blood collection system, illustrating the needle shield shield/needle guard device 20 with internal protrusion 27 in ready position to be positively locked onto the forward end of extended housing 35. FIG. 9 is a longitudinal section in FIG. 8 through line 9—9 revealing the inner protrusion 27 located on the inner distal wall of the needle shield/needle guard device 20, the cylindrical housing 26, and the pull-off tab 22 (with handle 23) which is attached to the cylindrical housing 26 on a weakened annular zone 25. FIG. 10 is a longitudinal section of the internal protrusion 27 in FIG. 9 through line 10—10 illustrating the internal protrusion 27.

FIG. 11 is a fragmented side enlargement of the front end of the extended housing 35 along line 11—11 of FIG. 8. This illustrates the groove system on the extended housing 35, and the longitudinal ridges 36 on the extended housing 35. Attachment of the needle shield/needle guard device 20 to the extended housing 35 occurs by sliding the internal protrusion 27 of the needle shield/needle guard device 20 over the funneled lead-in sloping groove 37, until the internal protrusion 27 slip-fits complementarily into the first extended lock position 42. The internal protrusion 27 is then positioned within three retaining walls of the first extended lock position 42 which are comprised of the horizontal retaining wall 34 and two contiguous retaining walls 32a and 32b. The complementary fitting of the internal protrusion 27 within the three retaining walls (32a, 32b, 34) of the first extended lock position 42 provides a positive locking means in three directions (forward, clockwise and counterclockwise) for the needle shield/needle guard device 20 in relation to the extended housing 35. Unintentional retraction of the cylindrical housing 26 of the needle shield/needle guard device 20 in relation to the extended housing 35 is prevented by a friction fit of the internal protrusion 27 within the first extended lock position 42 and the presence of the constricting bead 41 of the first extended lock position 42.

FIG. 11 also reveals the step-down access groove 43 and the longitudinal groove 45 FIG. 13 is a cross-sectional view along line 13—13 of FIG. 11 and illustrates the deeper groove depth of the longitudinal groove 45 as compared to the more shallow groove depth of the step-down access groove 43. In FIG. 11, these differential groove depths facilitate the retraction of the internal protrusion 27 from the first extended lock position 42 into the longitudinal groove 45 after the internal protrusion 27 has been intentionally moved over the constricting bead 41 of the first extended lock position 42.

FIG. 11 also illustrates the four retaining walls of the second extended lock position 47. When the internal protrusion 27 is locked in the second extended lock position 47, it is positioned within these four retaining walls comprised of the horizontal retaining wall 34 and three other retaining walls (48a, 48b, 48c). These retaining walls provide a positive locking means to prevent forward, backward, clockwise and counterclockwise rotation of the cylindrical housing 26 in relation to the extended housing 35.

FIG. 12 is a cross-sectional view of FIG. 11 along line 12—12 and reveals the funneled lead-in groove 37, two retaining walls 32a and 32b of the first extended lock position 42 forming acute angles with the floor of the first extended lock position 42, the longitudinal groove 45, and the retaining walls 48a and 48b which form acute angles with the floor of the second extended lock position 47.

FIG. 14 is an enlarged partial isometric view of the double-ended needle assembly 11 without the needle shield/needle guard device 20 for the first embodiment 8 of the evacuated blood collection system. This illustrates a fragmented view of the extended housing 35, the needle 56 housed in the extended housing 35, the double external protrusions 54, the longitudinal groove 45, double lead-in external threads 53, and the self-recoverable elastic sheath 55 covering the second needle 56.

FIG. 15 is an enlarged partial isometric view of the front end 61 of the container holder 60 for the first embodiment 8 of the evacuated blood collection system. This illustrates the double notches 63, the double lead-in internal mating threads 64, the longitudinal groove 49 of the container holder 60, the horizontal groove 50, the constricting bead of the horizontal groove 51, and the retracted lock position 52. FIG. 16 is a cross-sectional view of FIG. 15 along line 16—16 illustrating the double horizontal grooves 50, constricting bead of the horizontal groove 51 and the retracted lock position 52.

Referring back to FIG. 2, the primary locking means for the double-ended needle assembly 11 into the front end 61 of the container holder 60 occurs by engagement of the double lead-in external threads 53 into the double lead-in internal mating threads 64. In FIGS. 14 and 15, a secondary locking means occurs when the double external protrusions 54 seat inside the double notches 63. The secondary locking means also provide for a simultaneous alignment of the longitudinal groove 45 on the extended housing 35 with the longitudinal groove 49 on the front end 61 of the container holder 60.

Referring back to FIG. 2, this illustration reveals the working arrangement of the components of the first embodiment 8 of the evacuated blood collection system. The components consist of the double-ended needle assembly 11, the container holder 60 and the evacuated container 70. The container holder 60 is comprised of the narrowed diameter front end 61, and the wide girth body 62 of the container holder 60. The evacuated container 70 is comprised of a tube 71 and stopper 72. The double-ended needle assembly 11 is attached to the front end 61 of the container holder 60 by grasping and rotating the needle shield/needle guard device 20 clockwise so as to engage the double-lead-in external threads 53 into the double lead-in internal mating threads 64 on the front end 61 of the container holder 60 until the double external protrusions 54 seat inside the double notches 63 (see FIG. 17 for detail illustrating the engagement of the external protrusions 54 into the notches 63). In FIG. 2, the second needle 56 covered by the self-recoverable elastic sheath 55 extends rearward inside the wide girth body 62 of the container holder 60. The stopper 72 of the evacuated container 70 can then be engaged into the second needle 56 inside the container holder 60.

FIG. 18 illustrates the first embodiment 8 of the evacuated blood collection system with attachment of the double-ended needle assembly 11 to the container holder 60 and with the needle shield/needle guard device 20 positively locked in the first extended lock position 42. FIG. 18A is a cross-sectional view along line 18A—18A of FIG. 18 and reveals the internal protrusion 27 positioned into the first extended lock position 42. In FIG. 18, the needle shield/needle guard device 20 with the pull-off tab 22 intact functions as a needle shield to prevent contamination of the enclosed first needle 15. In order to exteriorize the first needle 15, the pull-off tab 22 must be removed from the weakened annular zone 25 of attachment to the cylindrical housing 26, causing formation of an aperture 30 on the front end of the cylindrical housing 26. The cylindrical housing 26 with the pull-off tab 22 removed is now in ready position to exteriorize the first needle 15 and thus function as a needle guard.

In FIG. 19, the cylindrical housing 26 with the pull-off tab 22 removed is shown retracted which exposes the first needle 15 for venipuncture usage. This maneuver occurs (see FIGS. 14 and 15) by retracting the internal protrusion 27 of the cylindrical housing 26 over the constricting bead 41 into the step-down access groove 43, then into the longitudinal groove 45 on the extended housing 35, then to the longitudinal groove 49 of the container holder, to the horizontal groove 50, over the constricting bead 51 of the horizontal groove and then into the retracted lock position 52. When the internal protrusion 27 is positioned into the retracted lock position 52, the internal protrusion 27 is positively locked so that it can not move forward, backwards or clockwise in relation to the front end 61 of the container holder 60.

It is to be understood that the design of this invention could include a second or more internal protrusion 27 on the cylindrical housing 26 with a second or more groove system on the extended housing 35 arranged at strategic locations so as to improve the stabile attachment and mobility of the cylindrical housing 26 on the extended housing 35 and front end 61 of the container holder 60.

FIG. 20 illustrates the first embodiment 8 of the evacuated blood collection system in which the cylindrical housing 26 of the needle shield/needle guard device 20 is retracted so as to expose the first needle 15 during venipuncture use. The second needle 56 has punctured through the stopper 72 into the evacuated container 70. FIG. 21 is a longitudinal section in FIG. 20 through line 21—21. A tertiary locking means for attachment of the double-ended needle assembly 11 to the container holder 60 occurs when the cylindrical housing 26 is retracted on the extended housing 35 to the front end 61 of the container holder 60. This occurs when the inner surface 19 of the front end of the cylindrical housing 26 with a small aperture 30 approximates the larger diameter forward end 31 of the extended housing 35 and the internal protrusion 27 is moved into the retracted lock position 52 on the front end 61 of the container holder 60. FIG. 21 also illustrates the extended housing 35 of the first embodiment 8 of the evacuated blood collection system which provides a length extension between the first needle 15 used to withdraw blood and the wide girth body 62 of the container holder 60. The length extension permits the user to direct the needle into a blood vessel at a more shallow or acute angle in respect to the planar surface of the skin and thus minimize the change of piercing through the other side of the blood vessel wall.

After venipuncture usage, the first embodiment 8 of the evacuated blood collection system can function as a needle guard, in which the cylindrical housing 26 can be re-extended back on the extended housing 35 into the second extended lock position 47 (see FIG. 14 and FIG. 15), and thereby re-cover the used first needle 15 with the cylindrical housing 26 from behind the needle point of the first needle 15. This occurs by moving the internal protrusion 27 out of the retracted lock position 52, over the constricting bead 51 into the horizontal groove 50, to the longitudinal groove 49 of the container holder, then to the longitudinal groove 45 of the extended housing, over the retaining wall 48a into the second extended lock position 47 which positively locks the cylindrical housing 26 in four directions (forward, backwards, clockwise and counterclockwise) in relation to the extended housing 35. It is noteworthy that the deeper groove depth of the longitudinal groove 45 compared to the more shallow step-down access groove 43 (see FIG. 13) facilitates the movement of the internal protrusion 27 into the second extended lock position 47. In FIG. 12, once the internal protrusion 27 of the cylindrical housing 26 is moved into the second extended lock position 47, the cylindrical housing 26 is positively locked so that it can never be retracted again to re-expose the needle 15. In (FIGS. 14 and 15), after the internal protrusion 27 has been positively locked into the second extended lock position 47, counterclockwise rotation on the cylindrical housing 26 will not move the cylindrical housing 26 in relation to the extended housing 35, but will cause the double external protrusions 54 to unseat from the double notches 63, permitting the disengagement of the double-ended needle assembly 11 from the container holder 60 by the counterclockwise unwinding of the external threads 53 from the internal mating threads 64.

FIGS. (22–26) refer to the second 8' embodiment of the evacuated blood collection system FIG. 22 illustrates a sterile container holder 10' for the second embodiment 8' comprised of the second needle shield 12' and the needle shield/needle guard device 20'. FIG. 23 illustrates the second embodiment 8' of the evacuated blood collection system comprised of the double-ended needle assembly 11' and the extended front end 61' of the container holder 60'. In FIG. 23, the essential difference of the second embodiment 8' compared to the first embodiment 8 of the evacuated blood collection system (see FIG. 2) is the extended front end 61' of the container holder 60' and the shortened housing 35' of the double-ended needle assembly 11'. The longitudinal groove 49' of the container holder 60' is longer in the second embodiment 8' by virtue of the extended front end 61' of the container holder 60'. Attachment of the double-ended needle assembly 11' to the container holder 60' occurs by the previously described primary and secondary locking means for the preferred embodiment 8 of the evacuated blood collection system. FIG. 24 illustrates the shortened housing 35' of the double-ended needle assembly 11', external threads 53', and grooves analogous to those in the first embodiment 8 of the evacuated blood collection system. The needle shield/needle guard device 20' (see FIG. 23) can function as a needle shield covering the sterile first needle 15' when the internal protrusion 27' is positively locked (see FIG. 24) into the first extended lock position 42' on the housing 35' by the same means as described for the first embodiment 8 of the evacuated blood collection system. The elements of the groove system are essentially the same as described for the first embodiment 8 of the evacuated blood collection system. FIG. 25 illustrates the removal of the pull-off tab 22' from the weakened annular zone 25' of attachment to the cylindrical housing 26' and the retraction of the cylindrical housing 26' on the extended front end 61' of the container holder 60'. This maneuver occurs as described for the first embodiment 8 of the evacuated blood collection system. FIG. 26 is a longitudinal section along line 26—26 in FIG. 25. It illustrates the tertiary locking of the double-ended needle assembly 11' to the container holder 60' as described for the first embodiment 8 of the evacuated blood collection system (see FIG. 21).

After use of the first needle 15' for venipuncture, the cylindrical housing 26' is re-extended back into the second extended lock position 47' (see FIG. 24) as described for the first embodiment 8 of the evacuated blood collection system, so that the cylindrical housing 26' can function as a needle guard which can re-cover the used first needle 15' from behind the needle point of the first needle 15'. The double-ended needle assembly 11' can then be unfastened from the container holder 60' as described for the preferred embodiment 8 of the evacuated blood collection system.

FIGS. (27 to 30) illustrate the first embodiment of the detachable needle assembly 90 for a hypodermic syringe 80. In FIG. 28, the detachable needle assembly 90 is secured to the hypodermic syringe 80 by means of a luer-lock. This invention can also be adapted so that other securing means could fasten the detachable needle assembly 90 to the hypodermic syringe 80. FIG. 27 illustrates an isometric view of the preferred embodiment of the detachable needle assembly 90. The detachable needle assembly 90 is comprised of a needle shield/needle guard device 20" with a cylindrical housing 26" and a pull-off tab 22", an extended housing 35", a luer-lock retainer wall 84, and the luer-lock thread 83 on the distal end of the needle hub 87. In FIG. 28, the needle shield/needle guard device 20" can function as a needle shield covering the sterile needle 91 when the internal protrusion 27" is moved over the funneled lead-in groove 37" to slip-fit complementarily into the first extended lock position 42" on the extended housing 35". In this position, the needle shield/needle guard device 20" is prevented from moving forward, clockwise or counterclockwise in relation to the extended housing 35". The entire groove system on the needle assembly 90 is comprised of a funneled lead-in groove 37", the first extended lock position 42", constricting bead 41" of the first extended lock position 42", longitudinal groove 45", constricting bead 51" of the retracted lock position 57 and the retracted lock position 57. FIG. 28 also illustrates in more detail other components of the first embodiment of the detachable needle assembly 90 which include the luer-lock retainer 84, and the luer-lock thread 83. The front end 85 of the syringe 80 is also illustrated with the cone fit 81 and the internal luer-lock mating threads 82. The detachable needle assembly 90 is fastened to the front end 85 of the syringe 80 by clockwise rotation of the needle shield/needle guard device 20" to engage the luer-lock thread 83 into the internal luer-lock mating threads 82 and slip-fitting of the external surface of the cone 81 into the internal surface 89 of the needle hub 87. The clockwise rotation of the needle shield/needle guard device 20" does not move the needle shield/needle guard device 20" clockwise in relation to the extended housing 35" by virtue of the positive locks as described. Unnecessary extra tightening of the pressure fit luer-lock is prevented when the distal surface 88 of the luer retainer wall 84 approximates the proximal surface 86 of the front end 85 of the syringe 80, thereby providing a constant tightening pressure of the luer-lock.

In FIG. 28, when the cylindrical housing 26" of the needle shield/needle guard device 20" is locked into the first extended lock position 42", unintentional retraction of the cylindrical housing 26" on the extended housing 35" is prevented by the resistance created by the friction fit of the internal protrusion 27" into the first extended lock position 42" and by the constricting bead 41" distal to the first extended lock position 42". When the pull-off tab 22" is removed from the cylindrical housing 26", the cylindrical housing 26" can be intentionally retracted into the retracted lock position 57 by moving the internal protrusion 27" over the constricting bead 41" to the longitudinal groove 45", over the constricting bead 51" into the retracted lock position 57. In that position, the internal protrusion 27" is positively locked so that the the cylindrical housing 26" is prevented from moving backward, clockwise and counterclockwise in relation to the extended housing 35". FIG. 29 is an isometric view illustrating exteriorization of the sterile needle 91 by the retraction of the cylindrical housing 26" on the extended housing 35" of the detachable needle assembly 90. FIG. 30 is a longitudinal section along line 30—30 of FIG. 29 and illustrates the retraction of the cylindrical housing 26" on the extended housing 35" and the distal surface 88 of the luer retainer wall 84 approximating the proximal surface 86 of the front end 85 of the syringe 80. FIG. 30 also illustrates the engagement of the external surface of the cone 81 into the internal surface 89 of the needle hub 87. The extended housing 35" provides a length extension between the needle 91 and the wide diametered syringe barrel 79. The length extension permits the user to direct the needle into a blood vessel at a more shallow or acute angle in respect to the planar surface of the skin and thus minimize the chance of piercing through the other side of the blood vessel wall.

Following usage of the needle 91 (see FIG. 28), the cylindrical housing 26" can function as a needle guard which is capable of re-extending back into the first extended lock position 42" on the extended housing 35" of the detachable needle assembly 90, and thereby allow the user to safely re-cover the used needle 91 by moving the cylindrical housing 26" from behind the needle point. This maneuver occurs (see FIG. 28) by reversing the sequence of movements of the internal protrusion 27" of the cylindrical housing 26" back into the first extended lock position 42". Alternatively, the user of this invention can elect to retract the cylindrical housing 26", fill the syringe with liquid medicament, and then delay injecting the liquid medicament by re-extending the cylindrical housing 26" back into the first extended lock position 42" to re-cover the sterile needle 91. The cylindrical housing 26" can then be retracted again to exteriorize the needle 91 to inject the medicament, and then the cylindrical housing 26" can be re-extended again to the first extended lock position 42" to re-cover the used needle 91. Retraction and extension of the cylindrical housing 26" in relation to the extended housing 35" of the detachable needle assembly 90 can occur ad-finitum.

The detachable used needle assembly 90 is unfastened from the front end 85 of the syringe 80 by counterclockwise rotation on the cylindrical housing 26". The counterclockwise rotation on the cylindrical housing 26" does not move the cylindrical housing 26" counterclockwise in relation to the extended housing 35" by virtue of the described positive locks while the internal protrusion 27" is locked into the first extended lock position 42", thereby providing coverage of the used needle 91 with the cylindrical housing 26" when the detachable needle assembly 90 is unfastened from the syringe 80. The counterclockwise rotation of the cylindrical housing 26" can overcome the luer-lock since the luer-lock retainer wall 84 prevented over-tightening between the luer lock thread 83 into the luer lock internal mating threads 82 and the contact between the slip-fitting surfaces of the external surface of the cone 81 and the internal surface 89 of the needle hub 87.

Depending on manufacturer stipulations, it is to be understood that the groove systems used for the first embodiment 8 and second embodiment 8' of the evacuated blood collection system could be reciprocally exchanged for the groove system used for the first embodiment of the needle assembly 90 for a hypodermic syringe.

It is to be understood that the form of the invention herewith shown and described is to be taken as the preferred embodiments. Various changes may be made in the shape, size, and arrangement of parts, for example: equivalent elements may be substituted for those illustrated and described herein, parts may be reversed and certain features of the invention may be utilized independently of the use of other features all without departing from the spirit or scope of the invention as defined in the subjoining claims.

We claim:

1. A first embodiment of an evacuated blood collection system with a combination needle shield/needle guard device positively locked onto a double-ended needle assembly, the invention comprising;

said evacuated blood collection system with said double-ended needle assembly comprising first needle, second needle, housing having a forward end and a rear end, said first needle extending outwardly from forward end of said housing, and said first needle adapted for insertion into a patient's blood vessel, said second needle extending outwardly from rear end of said housing, said second needle enveloped by self-recoverable elastic sheath, said second needle adapted for insertion into stopper of evacuated container;

a means within said housing of double-ended needle assembly for directing fluid flow unidirectionally from said first needle to said second needle which is engaged into said evacuated container;

threads on rear exterior of said housing of double-ended needle assembly, said threads with double lead-in threads;

container holder with internal mating threads on its forward end, said internal mating threads with double lead-in threads;

the improvements of our invention for said first embodiment of an evacuated blood collection system comprising;

said double-ended needle assembly with extended housing between said first needle extending outwardly from forward end of said extended housing and said second needle extending from rear end of said extended housing, groove system on said extended housing, said extended housing with double external protrusions strategically located on rear exterior of said extended housing;

a needle shield/needle guard device comprising a hollow cylindrical housing sealed at its proximal end with an integral pull-off tab, an internal protrusion extending internally from distal inner wall of said cylindrical housing;

a means for positive locking said needle shield/needle guard device into first extended lock position of said extended housing of double-ended needle assembly which prevents the forward clockwise and counterclockwise rotation of said needle shield/needle guard device in relation to front end of said extended housing;

a means for said needle shield/needle guard device as a needle shield to enclose said first sterile needle;

a sterile package container for said double-ended needle assembly;

a means for removal of said double-ended needle assembly with positively locked needle shield/needle guard device from said sterile package container;

a container holder with duplicate groove systems and notches located at strategic distances from each other;

a primary means for engaging and securing said double-ended needle assembly to said container holder by a simultaneous clockwise rotation of said needle shield/needle guard device and said extended housing without separate clockwise rotation of said needle shield/needle guard device in relation to said extended housing of double-ended needle assembly;

a means for alignment of longitudinal groove on said extended housing of double-ended needle assembly with one of two longitudinal grooves of said container holder;

said means for alignment of said longitudinal grooves also providing a secondary locking means for securing of said double-ended needle assembly to said container holder;

a means for aperture formation on proximal end of said cylindrical housing of said needle shield/needle guard device;

a means to provide resistance for retraction of said cylindrical housing of said needle shield/needle guard device in relation to said extended housing of double-ended needle assembly;

a means for said cylindrical housing as a needle guard after said aperture has been formed, such that said cylindrical housing can retract distally into retracted lock position on said container holder, uncovering said first needle;

a means provided to facilitate movement of said cylindrical housing from said first extended lock position to said retracted lock position;

a means for positively locking said cylindrical housing into said retracted lock position which prevents the forward, backward, and clockwise rotation of said cylindrical housing in relation to front end of said container holder;

a tertiary means for locking said double-ended needle assembly to said container holder;

a length extension of said extended housing of double-ended needle assembly providing means for shallow or acute angulation to insert said first needle into planar surface of skin and blood vessel;

a means for said cylindrical housing as a needle guard, such that said cylindrical housing can re-extend into second extended lock position on said extended housing of double-ended needle assembly, re-covering said first needle from behind needle point of said first needle;

a means provided to facilitate movement of said cylindrical housing from said retracted lock position to said second extended lock position;

a means for positive locking said cylindrical housing into said second extended lock position on said double-ended needle assembly which prevents the forward, backward, clockwise and counterclockwise rotation of said cylindrical housing in relation to said extended housing of double-ended needle assembly; and a means for disengaging said double-ended needle assembly from said container holder while maintaining coverage of said first needle with said cylindrical housing.

2. The invention as set forth in claim 1 with said means for positive locking said needle shield/needle guard device into said first extended lock position of said extended housing of double-ended needle assembly which prevents the forward, clockwise or counterclockwise rotation of said needle shield/needle guard device in relation to said extended housing, said means comprising said internal protrusion of said needle shield/needle guard device which can slide over funneled lead-in sloping groove on forward end of said extended housing, until said internal protrusion slip-fits complementarily into positively locking retaining walls of said first extended lock position.

3. The invention as set forth in claim 1, and particularly when said needle shield/needle guard device has been positively locked onto forward end of said extended housing of double-ended needle assembly into said first extended lock position, wherein said needle shield/needle guard device is provided with means as a needle shield to enclose said sterile first needle attached to said extended housing of double-ended needle assembly, said means comprising said hollow cylindrical housing of needle shield/needle guard device which is sealed at its proximal end by said pull-off tab integrally attached at weakened annular zone on the proximal end of said cylindrical housing.

4. The invention as set forth in claim 1 with said means for said needle shield/needle guard device as part of said sterile package container for said double-ended needle assembly, said means for said sterile package container comprising said needle shield/needle guard device which covers said first sterile needle, a second needle shield which covers said second sterile needle and sealing tape which joins and seals said needle shield/needle guard device to said second needle shield covering said second needle.

5. The invention as set forth in claim 1 for said primary locking means of said double-ended needle assembly to said container holder by simultaneous clockwise rotation of said needle shield/needle guard device and said extended housing of double-ended needle assembly without separate clockwise rotation of said needle shield/needle guard device in relation to said extended housing, said means comprising said needle shield/needle guard device positively locked onto said extended housing in said first extended lock position and said double lead-in external threads on rear exterior of said extended housing which can engage and secure with said double lead-in internal mating threads within forward end of said container holder, such that clockwise rotation of said needle shield/needle guard device can engage and secure said double lead-in external threads into said lead-in internal mating threads without separate clockwise rotation of said needle shield/needle guard device in relation to said extended housing.

6. The invention as set forth in claim 1 with a means for alignment of said longitudinal groove on said extended housing of double-ended needle assembly with said one of two longitudinal grooves located on front end of said container holder, said means provided by said double external protrusions strategically located on said extended housing of double-ended needle assembly which seat into strategically located said double notches on front end of said container holder.

7. The invention as set forth in claim 5 with said alignment means also providing secondary locking means for securing of said double-ended needle assembly to said container holder, said secondary locking means provided by seating of said double external protrusions on said extended housing of double-ended needle assembly into said double notches on front end of said container holder.

8. The invention as set forth in claim 1 with means for aperture formation on proximal end of said cylindrical housing, said means comprising said integral pull-off tab which can be removed from said weakened annular zone on said proximal end of said cylindrical housing of said needle shield/needle guard device.

9. The invention as set forth in claim 1 with a means for resisting retraction of said cylindrical housing in relation to said extended housing of double-ended needle assembly, said means provided by friction fit of said internal protrusion into said first extended lock position and the constricting bead distal to said first extended lock position which impedes free access of said internal protrusion into step-down access groove.

10. The invention as set forth in claim 1 with said cylindrical housing as a needle guard which is responsive to retraction in relation to said extended housing of double-ended needle assembly, and more particularly with said pull-off tab removed from said cylindrical housing, such that said internal protrusion of cylindrical housing can move in said groove system from said first extended lock position over said constricting bead into said step-down access groove, to said longitudinal groove on said extended housing, to said longitudinal groove on front end of said container holder, to horizontal groove into said retracted lock position, uncovering said sterile first needle enclosed by said cylindrical housing.

11. The invention as set forth in claim 1 with means provided for facilitation of movement of said cylindrical housing from said first extended lock position to said retracted lock position, said means comprising differential groove depths of said step-down access groove and said longitudinal grooves on said extended housing and said container holder, such that said internal protrusion can move preferentially from shallower groove of said step-down access groove into deeper said longitudinal grooves.

12. The invention as set forth in claim 1 with a means for positively locking said cylindrical housing into said retracted lock position on front end of said container holder which prevents forward, backward, and clockwise rotation of said cylindrical housing in relation in front end of said container holder, said means comprising said internal protrusion of said cylindrical housing which slip-fits complementarily into positively locking retaining walls of said retracted lock position.

13. The invention as set forth in claim 1 such that a tertiary locking means is provided for securing said double-ended needle assembly to said container holder, said means comprising the approximation of proximal end of said cylindrical housing with small said aperture to larger diameter of forward end of said extended housing of double-ended needle assembly and the engagement of said internal protrusion of said cylindrical housing into said retracted lock position on forward end of said container holder.

14. The invention as set forth in claim 1 with said cylindrical housing as a needle guard, in which said internal protrusion of said cylindrical housing is in said retracted lock position on forward end of said container holder, with said cylindrical housing responsive to extension movement in relation to forward end of said container holder and said extended housing of double-ended needle assembly, such that said internal protrusion of said cylindrical housing can move in said groove systems from said retracted lock position to said horizontal groove to said longitudinal grooves on front end of said container holder and said extended housing, to said second extended lock position, re-covering said first needle with said cylindrical housing from behind said needle point of said first needle.

15. The invention as set forth in claim 1 with means provided for facilitation of movement of said cylindrical housing from said retracted lock position to said second extended lock position, said means comprising differential groove depths of said step-down access groove and said longitudinal grooves on said extended housing and said container holder, such that said internal protrusion will preferentially remain in deeper said longitudinal grooves as compared to moving up into shallower groove of said step-down access groove.

16. The invention as set forth in claim 1 with a means for positive locking said cylindrical housing into said second extended lock position which prevents forward, backward, clockwise and counterclockwise rotation of said cylindrical housing in relation to said extended housing of double-ended needle assembly, said means comprising said internal protrusion which slip-fits complementarily into positively locking retaining walls of said second extended lock position.

17. The invention as set forth in claim 1 for means to disengage said double-ended needle assembly from said container holder while maintaining coverage of said first needle with said cylindrical housing, said means comprising said cylindrical housing positively locked into said second extended lock position, such that counterclockwise rotation of said cylindrical housing can overcome said primary and secondary locking means between said double-ended needle assembly and said container holder without separate counterclockwise rotation of said cylindrical housing out of said second extended lock position, maintaining coverage of said first used needle with said cylindrical housing when said double-ended needle assembly is disengaged from said container holder.

18. A second embodiment of an evacuated blood collection system with a combination needle shield/needle guard device positively locked onto a double-ended needle assembly, the invention comprising;
  said evacuated blood collection system with said double-ended needle assembly comprising, first needle, second needle, housing having a forward end and a rear end, said first needle extending outwardly from forward end of said housing, and said first needle adapted for insertion into a patient's blood vessel, said second needle extending outwardly from rear end of said housing, said second needle enveloped by self-recoverable elastic sheath, said second needle adapted for insertion into stopper of evacuated container;
  a means within said housing of double-ended needle assembly for directing fluid flow unidirectionally from said first needle to said second needle, which is engaged into said evacuated container;
  threads on rear exterior of said housing of double-ended needle assembly, said threads with double lead-in threads;
  container holder with internal mating threads on its forward end, said internal mating threads with double lead-in threads;
  the improvement of our invention for said second embodiment of an evacuated blood collection system comprising;
  said housing of double-ended needle assembly with groove system on said housing, said housing with double external protrusions strategically located on rear end of said housing;
  a needle shield/needle guard device comprising a hollow cylindrical housing sealed at its proximal end with an integral pull-off tab, an internal protrusion extending internally from distal inner wall of said cylindrical housing;
  a means for positively locking said needle shield/needle guard device into first extended lock position of said housing of double-ended needle assembly which prevents the forward, clockwise and counterclockwise rotation of said needle shield/needle guard device in relation to said housing of double-ended needle assembly;
  a means for said needle shield/needle guard device as a needle shield to enclose said first sterile needle;
  a sterile package container for said double-ended needle assembly;
  a means for removal of said double-ended needle assembly with positively locked needle shield/needle guard device from said sterile package container;
  a container holder with extended front end of said container holder, said extended front end of container holder with said internal mating threads on its forward end, duplicate groove systems and notches located at strategic distances from each other on said extended front end of container holder;
  a primary means for engaging said securing said double-ended needle assembly to said container holder by a simultaneous clockwise rotation of said needle shield/needle guard device and said housing of double-ended needle assembly without separate clockwise rotation of said needle shield/needle guard device in relation to said housing;

a means for alignment of longitudinal groove on said housing of double-ended needle assembly with one of two longitudinal grooves on said extended front end of container holder;

said means for alignment of said longitudinal grooves also providing a secondary locking means for securing of said double-ended needle assembly to said container holder;

a means for aperture formation on proximal end of said cylindrical housing of said needle shield/needle guard device;

a means to provide resistance for retraction of said cylindrical housing in relation to said housing of double-ended needle assembly;

a means for said cylindrical housing as a needle guard after said aperture has been formed, such that said cylindrical housing can retract distally into retracted lock position on said container holder, uncovering said first sterile needle;

a means provided to facilitate movement of said cylindrical housing from said first extended lock position to said retracted lock position;

a means for positively locking said cylindrical housing into said retracted lock position which prevents the forward, backward, and clockwise rotation of said cylindrical housing in relation to said extended front end of said container holder;

a tertiary means for locking said double-ended needle assembly to said container holder;

a length extension of said extended front end of container holder providing means for shallow or acute angulation to insert said first needle into planar surface of skin and blood vessel;

a means for said cylindrical housing as a needle guard, such that said cylindrical housing can reextend into second extended lock position on said housing of double-ended needle assembly, re-covering said first needle from behind needle point of said first needle;

a means provided to facilitate movement of said cylindrical housing from said retracted lock position to said second extended lock position;

a means for positively locking said cylindrical housing into said second extended lock position on said housing of double-ended needle assembly which prevents the forward, backward, clockwise and counterclockwise rotation of said cylindrical housing in relation to said housing of double-ended needle assembly; and a means for disengaging said double-ended needle assembly from said container holder while maintaining coverage of said first needle with said cylindrical housing.

19. The invention as set forth in claim 16 with said means for positive locking said needle shield/needle guard device into said first extended lock position of said housing of double-ended needle assembly which prevents the forward, clockwise and counterclockwise rotation of said needle shield/needle guard device in relation to said housing of double-ended needle assembly, said means comprising said internal protrusion of said needle shield/needle guard device which can slide over funneled lead-in sloping groove on forward end of said housing, until said internal protrusion slip-fits complementarily into positively locking retaining walls of said first extended lock position.

20. The invention as set forth in claim 16 and particularly when said needle shield/needle guard device has been positively locked onto said housing of double-ended needle assembly into said first extended lock position, wherein said needle shield/needle guard device is provided with means as a needle shield to enclose said sterile first needle attached to said housing of double-ended needle assembly, said means comprising said hollow cylindrical housing of needle shield/needle guard device which is sealed at its proximal end by pull-off tab integrally attached at weakened annular zone on the proximal end of said cylindrical housing.

21. The invention as set forth in claim 16 with said means for said needle shield/needle guard device as part of said sterile package container for said double-ended needle assembly, said means for said sterile package container comprising said needle shield/needle guard device which covers said first sterile needle, a second needle shield which covers said second sterile needle and sealing tape which joins and seals said needle shield/needle guard device to said second needle shield covering said second needle.

22. The invention as set forth in claim 16 for said primary locking means of said double-ended needle assembly to said container holder by simultaneous clockwise rotation of said needle shield/needle guard device and said housing of double-ended needle assembly without separate clockwise roatation of said needle shield/needle guard device in relation to said housing, said means comprising said needle shield/needle guard device positively locked onto said housing in said first extended lock position and said double lead-in external threads on rear exterior of said housing which can engage and secure with said double lead-in internal mating threads within said extended front end of container holder, such that clockwise rotation of said needle shield/needle guard device can engage and secure said double lead-in external threads into said lead-in internal mating threads without separate clockwise rotation of said needle shield/needle guard device in relation to said housing of double-ended needle assembly.

23. The invention as set forth in claim 16 with a means for alignment of said longitudinal groove on said housing of double-ended needle assembly with one of two longitudinal grooves located on said extended front end of container holder, said means provided by double external protrusions strategically located on said housing of double-ended needle assembly which seat into strategically located said double notches on said extended front end of container holder.

24. The invention as set forth in claim 21 with said alignment means also providing secondary locking means for securing of said double-ended needle assembly to said container holder, said secondary locking means provided by seating of said double external protrusions on said housing of double-ended needle assembly into said double notches on said extended front end of container holder.

25. The invention as set forth in claim 16 with means for aperture formation on proximal end of said cylindrical housing, said means comprising said integral pull-off tab which can be removed from attachment at said weakened annular zone on said proximal end of said cylindrical housing of said needle shield/needle guard device.

26. The invention as set forth in claim 16 with a means for resisting retraction of said cylindrical housing in relation to said housing of double-ended needle assembly, said means provided by friction fit of said internal protrusion into said first extended lock position and the constricting bead distal to said first extended lock position which impedes free access of said internal protrusion into step-down groove.

27. The invention as set forth in claim 16 with said cylindrical housing as a needle guard which is responsive to retraction in relation to said housing of double-ended needle assembly and said extended front end of container holder, and more particularly, with said pull-off tab removed from said cylindrical housing of said needle shield/needle guard device, such that said internal protrusion of cylindrical housing can move in said groove system from said first extended lock position over said constricting bead into said step-down access groove, to said longitudinal groove on said housing of double-ended needle assembly, to said longitudinal groove on said extended front end of container holder, to horizontal groove into said retracted lock position, uncovering said sterile first needle enclosed by said cylindrical housing.

28. The invention as set forth in claim 16 with means provided for facilitation of movement of said cylindrical housing from said first extended lock position to said retracted lock position, said means comprising differential groove depths of said step-down access groove and said longitudinal grooves on said housing of double-ended needle assembly and said extended front end of container holder, such that said internal protrusion can move preferentially from shallower groove of said step-down access groove into deeper said longitudinal grooves.

29. The invention as set forth in claim 16 with a means for positively locking said cylindrical housing into said retracted lock position on said extended front end of container holder which prevents the forward, backward, and clockwise rotation of said cylindrical housing in relation to the said extended front end of container holder, said means comprising said internal protrusion of said cylindrical housing which slip-fits complementarily into positively locking retaining walls of said retracted lock position.

30. The invention as set forth in claim 16 such that a tertiary locking means is provided for securing of said double-ended needle assembly to said container holder, said means comprising the approximation of proximal end of said cylindrical housing with small said aperture to larger diameter of forward end of said housing of double-ended needle assembly and the engagement of said internal protrusion of said cylindrical housing into said retracted lock position on said extended front end of container holder.

31. The invention as set forth in claim 16 with said cylindrical housing as a needle guard, in which said internal protrusion of said cylindrical housing is in said retracted lock position on said extended front end of container holder, with said cylindrical housing responsive to extension movement in relation to said extended front end of container holder and said housing of double-ended needle assembly, such that said internal protrusion of cylindrical housing can move in said groove system from said retracted lock position to said horizontal groove to said longitudinal grooves on said extended front end of container holder and said housing of double-ended needle assembly, to said second extended lock position, re-covering said first needle with said cylindrical housing from behind said needle point of said first needle.

32. The invention as set forth in claim 16 with means provided for facilitation of movement of said cylindrical housing from said retracted lock position to said second extended lock position, said means comprising differential groove depths of said step-down access groove and said longitudinal grooves on said extended front end of container holder and said housing of double-ended needle assembly, such that said internal protrusion will preferentially remain in deeper said longitudinal grooves as compared to moving up into shallower groove of said step-down access groove.

33. The invention as set forth in claim 16 with a means for positively locking said cylindrical housing into said second extended lock position which prevents the forward, backward, clockwise and counterclockwise rotation of said cylindrical housing in relation to said housing of double-ended needle assembly, said means comprising said internal protrusion which slip-fits complementarily into positive locking retaining walls of said second extended lock position.

34. The invention as set forth in claim 16 for means to disengage said double-ended needle assembly from said container holder while maintaining coverage of said used first needle, said means comprising said cylindrical housing positively locked into said second extended lock position such that counterclockwise rotation of said cylindrical housing can overcome said primary and secondary locking means between said double-ended needle assembly and said container holder without separate counterclockwise rotation of said cylindrical housing out of said second extended lock position, maintaining coverage of said first needle with said cylindrical housing when said double-ended needle assembly is disengaged from said container holder.

35. A first embodiment of a detachable needle assembly for a hypodermic syringe, with a combination needle shield/needle guard device positively locked into said needle assembly, the invention comprising;
 said hypodermic syringe comprising syringe barrel and piston, said piston sliding inside said syringe barrel;
 the improvements for our invention for said hypodermic needle assembly and said hypodermic syringe comprising;
 said detachable needle assembly comprised of needle, an extended housing for said needle, a needle hub at distal end of said extended housing, a groove system on said extended housing;
 said needle shield/needle guard device comprising a hollow cylindrical housing sealed at its proximal end with an integral pull-off tab, an internal protrusion extending internally from distal inner wall of said cylindrical housing for engaging said groove system;
 a means for positively locking said needle shield/needle guard device into first extended lock position of said extended housing of needle assembly which prevents the forward, clockwise and counterclockwise rotation of said needle shield/needle guard device in relation to said extended housing of needle assembly;
 a means for said needle shield/needle guard device as a needle shield to enclose said sterile needle;
 said detachable needle assembly with securing means for attaching said needle hub on distal end of said extended housing into forward end of said syringe barrel;

a means to prevent over-tightening pressure of said securing means when said needle assembly is secured into forward end of said syringe barrel, thereby providing a constant tightening pressure of said securing means;

a means for aperture formation on proximal end of said cylindrical housing of said needle shield/needle guard device;

a means to provide resistance for retraction of said cylindrical housing in relation to said extended housing of needle assembly;

a means for said cylindrical housing as a needle guard after said aperture has been formed, such that said cylindrical housing can retract into retracted lock position on said extended housing of needle assembly, uncovering said needle;

a means for positively locking said cylindrical housing into said retracted lock position which prevents the backward, clockwise, and counterclockwise rotation of said cylindrical housing in relation to said extended housing of the needle assembly;

a means for said cylindrical housing as a needle guard, such that said cylindrical housing can re-extend into said first extended lock position, re-covering said needle from behind the needle point of said needle;

a means for said cylindrical housing as a needle guard to retract, uncovering said needle, and extend, re-covering said needle, ad-finitum in relation to said extended housing of needle assembly; and a means to disengage said needle assembly from said syringe barrel while maintaining coverage of said needle with said cylindrical housing.

36. The invention as set forth in claim 31 with said means for positively locking said needle shield/needle guard device into said first extended lock position on said extended housing of needle assembly which prevents the forward, clockwise or counterclockwise rotation of said needle shield/needle guard device in relation to said extended housing, said means comprising said internal protrusion of said needle shield/needle guard device which can slide over funneled lead-in sloping groove on forward end of said extended housing, until said internal protrusion slip-fits complementarily into positively locking retaining walls of said first extended lock position.

37. The invention as set forth in claim 31, and particularly when said needle shield/needle guard device has been positively locked onto front end of said extended housing of needle assembly into said first extended lock position, wherein said needle shield/needle guard device is provided with means as said needle shield to enclose said needle, said means comprising said hollow cylindrical housing of needle shield/needle guard device which is sealed at its proximal end by said pull-off tab integrally attached at weakened annular zone on the proximal end of said cylindrical housing.

38. The invention as set forth in claim 31 wherein said securing means includes a luer-lock and means to prevent over-tightening pressure of said luer-lock during securing of said needle assembly into front end of said syringe barrel, thereby providing a constant tightening of said luer-lock, said means comprising a luer-lock retainer wall approximately front end of said syringe barrel.

39. The invention as set forth in claim 31 with means for aperture formation on proximal end of said cylindrical housing of said needle shield/needle guard device, said means comprising said integral pull-off tab which can be removed from attachment at said weakened annular zone on said proximal end of said cylindrical housing.

40. The invention as set forth in claim 31 with a means for resisting retraction of said cylindrical housing in relation to said extended housing of needle assembly, said means provided by friction fit of said internal protrusion into said first extended lock position and the constricting bead distal to said first extended lock position which impedes free access of said internal protrusion into said longitudinal groove.

41. The invention as set forth in claim 31 with said cylindrical housing as said needle guard with means to retract said cylindrical housing from said first extended lock position to said retracted lock position, and more particularly with said pull-off tab removed from said cylindrical housing, said means provided by said cylindrical housing responsive to retraction movement such that said internal protrusion of cylindrical housing can move in said groove system from said first extended lock position over said constricting bead to said longitudinal groove, over said constricting bead into said retracted lock position, uncovering said sterile needle enclosed by said cylindrical housing.

42. The invention as set forth in claim 31 with a means for positively locking said cylindrical housing into said retracted lock position which prevents the backward, clockwise, or counterclockwise rotation of said cylindrical housing in relation to said extended housing of needle assembly, said means comprising said internal protrusion of cylindrical housing which slip-fits complementarily into positively locking retaining walls of said retracted lock position.

43. The invention as set forth in claim 31 with said cylindrical housing as said needle guard, with means to re-extend said cylindrical housing from said retracted lock position to said extended lock position, said means provided by said cylindrical housing responsive to extension movement such that said internal protrusion of cylindrical housing can move in said groove system from said retracted lock position over said constricting bead to said longitudinal groove, over said constricting bead to said first extended lock position, re-covering said needle with said cylindrical housing from behind said needle point of said needle.

44. The invention as set forth in claim 31 with a means for said cylindrical housing as a needle guard with means to retract ad-finitum, uncovering said needle, and re-extend ad-finitum, re-covering said needle, in relation to said extended housing of needle assembly, said means comprising said groove system with no positive locking retaining walls preventing the retraction movement of said internal protrusion of said cylindrical housing from said first extended lock position to said retracted lock position and no positive locking retaining walls preventing the extension movement of said internal protrusion of said cylindrical housing from said retracted lock position to said first extended lock position.

45. The invention as set forth in claim 31 with a means to disengage said needle assembly from said syringe barrel while maintaining coverage of said needle with said cylindrical housing, said means comprising said cylindrical housing positively locked into said first extended lock position, such that counterclockwise rotation of said cylindrical housing can overcome said constant tightening pressure of said securing means between said needle assembly and said syringe barrel without causing counterclockwise rotation of said cylindrical housing out of said first extended lock position, maintaining coverage of said needle with said cylindrical housing when said needle assembly is disengaged from said syringe.

* * * * *